United States Patent [19]

Andrews et al.

[11] Patent Number: 5,026,927
[45] Date of Patent: Jun. 25, 1991

[54] HYDROCRACKING OF CARBOHYDRATES MAKING GLYCEROL, GLYCOLS AND OTHER POLYOLS

[75] Inventors: Mark A. Andrews, Ridge, N.Y.; Stephen A. Klaeren, Corpus Christi, Tex.

[73] Assignee: The United States of America as represented by the United States Department of Energy, Washington, D.C.

[21] Appl. No.: 437,403

[22] Filed: Nov. 16, 1989

[51] Int. Cl.$^5$ .................. C07C 29/14; C07C 31/20; C07C 31/22; C07C 29/136
[52] U.S. Cl. .................................................. 568/863
[58] Field of Search ........................................ 568/863

[56] References Cited

U.S. PATENT DOCUMENTS

| | | |
|---|---|---|
| 3,030,429 | 4/1962 | Conradin et al. ............... 568/863 |
| 3,396,199 | 8/1968 | Kasehagen .................... 568/863 |
| 3,935,284 | 1/1976 | Kruse ........................... 568/863 |
| 3,963,788 | 6/1976 | Kruse et al. ................... 568/863 |
| 4,072,720 | 2/1978 | Haag et al. .................... 568/863 |
| 4,380,678 | 4/1983 | Sirkar ........................... 568/863 |
| 4,380,679 | 4/1983 | Arena ........................... 568/863 |
| 4,476,331 | 10/1984 | Dubeck et al. ................ 568/863 |

Primary Examiner—J. E. Evans
Attorney, Agent, or Firm—Margaret C. Bogosian; James W. Weinberger; William R. Moser

[57] ABSTRACT

A homogeneous process for hydrocracking of carbohydrates in the presence of soluble transition metal hydrogenation catalyst with the production of lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi.

14 Claims, No Drawings

HYDROCRACKING OF CARBOHYDRATES MAKING GLYCEROL, GLYCOLS AND OTHER POLYOLS

This invention was made with Government support under contract number DE-AC02-76CH00016, between the U.S. Department of Energy and Associated Universities, Inc. The Government has certain rights in the invention.

BACKGROUND OF THE INVENTION

The present invention is a process for the hydrocracking of carbohydrates in the presence of a homogeneous transition metal catalyst to give commercially important glycols.

In the past, conversions of this type have been carried out using heterogeneous metal catalysts at high temperatures, typically about 200° C., with hydrogen pressures over 500 psi, in the presence of promoters. For example, U.S. Pat. No. 4,496,780 disclosed the hydrocracking of carbohydrate polyols using a heterogeneous catalyst of a Group VIII metal such as ruthenium composited on a support and an alkaline earth metal oxide. The process requires a temperature of 150° to 250° C. and a pressure of 500-5,000 psig. U.S. Pat. No. 4,476,331 discloses hydrogenolysing of hydrogenated sugars to lower polyhydric alcohols using a supported, sulfided $RuCl_3$ catalyst and a base, at a temperature of 150°-300° C. and a hydrocarbon pressure of 500-5,000 psig. U.S. Pat. No. 4,401,823 describes the hydrogenolysis of plyhydroxylated compounds in the presence of a shaped carbonaceous prepolymer impregnated with a Group VIII metal such as ruthenium, at 175°-250° C. and 10-2,000 psi.

Other heterogeneous hydrogenation catalysts such as supported nickel, platinum or palladium used with bases in the hydrogenolysis of carbohydrates are described in U.S. Pat. Nos. 4,404,411 4,380,678, 3,396,199 and 3,030,429. Typical feedstocks are glucose or glucitol (sorbitol) and typical products are mixtures of ethylene glycol, propylene glycol and glycerol.

U.S. Pat. No. 2,209,055 discloses a process for cleaving monosaccharides in the presence of a tertiary amine and a Raney nickel catalyst in a solvent at a temperature of at lest 75° C. and a hydrogen pressure of at least 2,000 psi.

Heterogeneous catalysts form a separate phase from reactants and products and are generally solids. Homogeneous catalysts, in contrast to heterogeneous catalysts, can be dispersed in solution.

Soluble ruthenium complexes have been used as homogeneous catalysts for hydrogenation reactions. Linn, Jr., D. E. et al., *J. Am. Chem. Soc.*, 109, 2969-2974 (1987) discloses the hydrogenation of ketones and arenes in the presence of $RuH_4$-$(PPh_3)_3$ or $[RuH_3(PPh_3)_3]^-$ in tetrahydrofuran solution. U.S. Pat. No. 3,935,284 discloses homogeneous catalytic hydrogenation of sugars in the presence of a ruthenium triphenylphosphine complex and a strong acid. For example, fructose was hydrogenated to yield mannitol and glucitol. However, no carbohydrate hydrocracking has been previously undertaken or suggested using homogeneously catalyzed reactions.

Accordingly, it is an object of the present invention to provide a process for the hydrocracking or hydrogenolysis of carbohydriates using homogeneous catalysts under milder conditions than previously possible with better product selectivity, thereby reducing the costs associated with both substrate conversion and product purification.

SUMMARY OF THE INVENTION

The invention is a process for hydrocracking carbohydrates by bringing a carbohydrate substrate into contact with hydrogen in the presence of a soluble transition metal hydrogenation catalyst in solution at a temperature of from about 25° C. to about 200° C. Conversion rate and selectivity for hydrocracking over simple hydrogenation are improved with the addition of a strong base.

The invention is also a process for the production of lower polyhydric alcohols by contacting a monosaccharide with hydrogen in the presence of a soluble transition metal catalyst and a base at a temperature of from about 75° C. to about 125° C. and a pressure of about 100 to 500 psi hydrogen in an amide solvent.

The advantages achieved by the invention include the use of milder reaction conditions with respect to both temperature and pressure and greater selectivity for ethylene glycol and/or glycerol over propylene glycol.

For a better understanding of the present invention, together with other and further objects, reference is made to the following description and its scope will be pointed out in the appended claims.

DETAILED DESCRIPTION OF THE INVENTION

In the present invention, carbohydrates may be hydrocracked to yield glycols. Carbohydrate feedstocks which may be hydrocracked in accordance with the invention are monosaccharide aldose or ketose sugars such as fructose, sorbose, glucose, mannose, xylose, ribose, galactose and arabinose. Other feedstocks include carbohydrates such as glucitol, mannitol, xylitol, disaccharides such as sucrose, and high molecular weight polysaccharides such as starch and cellulose which can be converted to appropriate monosaccharide sugars either in situ or in a prior first stage pretreatment process.

Catalysts employed are homogeneous transition metal aldehyde or ketone hydrogenation catalysts of the Group VIII metals of the Periodic Table such as $H_2Ru(PPh_3)_4$, $H_2Ru(CO)(PPh_3)_3$, $H_3Ru(PPh_3)_3^{-1}$, $H_3Ir(PPh_3)_3$, $HMX(CO)(PPh_3)_n$ (M=Ru,Os; X=Cl,Br,$CH_3CO_2$: n=2,3), $RhCl(PPh_3)_3$, $HRh(PPh_3)_4$, $H_3Rh(PPhMe_2)_2(solvent)_2^{+1}$, and $RuCl_2(PPh_3)_3$. Hydrogenation catalysts with other metals such as Fe, Mn and Co can also be used. The catalysts are prepared by conventional known methods.

The catalyst need only be present in minimal amounts sufficient for process activity. Generally, the catalyst concentration will be at least about 0.001 mole percent of the substrate up to about 10 mole percent of the substrate, preferably from about 0.01 to about 5.0 mole percent of the substrate.

Both the reaction rate and selectivity for hydrocracking over simple hydrogenation, i.e., for lower glycols over hexitols, are enhanced by the addition of a cocatalyst or promoter. Suitable promoters are strong bases such as alkali metal hydroxides and basic salts, alkaline earth metal oxides, hydroxides and basic salts, alkoxides, and quaternary ammonium hydroxide not subject to Hofmann elimination, such as $(CH_3)_4NOH$. Representative bases are, for example, potassium, barium hydroxide, and sodium hydroxide. The amount of base employed can typically vary from about 0.01 to about 25 mole percent, preferably from about 0.2 to about 10 mole percent of the carbohydrate employed. However, large amounts of base, e.g. over 10 mole percent of the carbohydrate are less desirable because they can cause excessive degradation of the feedstock sugars.

The carbohydrate feedstock, catalyst and promoter are dissolved in a solvent. Suitable solvents are polar solvents that dissolve sugars but have low coordinating strength toward Group VIII metal complexes, typically amides such as N-methyl-2-pyrrolidinone and N,N-dimethylacetamide. Generally, fully alkylated amides are useful as solvents in the invention. Water can also be used if the metal catalyst is made soluble in water, for example by conversion to an anion or cation by any known method, commonly by sulfonating triphenylphosphine ligands using methods such as those reviewed by Joo, F., et al., *Journal of Molecular Catalysis*, 8, 369-383 (1980).

Instead of being dissolved in the solvent, the homogeneous catalyst may instead by immobilized by well-known means on a support such as phosphine derivatized polystyrene or silica, for example, by using a method disclosed by Pittman, C. U., Jr., *Comprehensive Organometallic Chemistry*, 8, 533-607 (1982). The catalyst may then be used in a fixed bed or fluidized bed process using any solvent compatible with the support and catalyst that dissolves the carbohydrate, e.g., water, alcohol, amide, etc.

The temperature and pressure are generally lower than those previously reported to be necessary when hydrocracking over heterogeneous catalysts. The carbohydrates is subjected to hydrocracking by treatment at a temperature of from about 25° C. to about 200° C., and a pressure of about 15 to about 3000 psi hydrogen in the presence of a soluble transition metal catalyst and optional base co-catalyst. The time of the reaction is not critical and depends on reaction kinetics which in turn depend on such factors as the type and amount of reactants, the temperature and the pressure. The time may be, for example, from about 1 to about 12 hours or more, and is generally at least about 15 minutes. The process is preferably carried out at a temperature of from about 50° C. to about 150° C., and more preferably from about 75° C. to about 125° C. and at pressures preferably of from about 100 to about 500 psi hydrogen. Advantageous results have been shown with temperatures as low as about 50° C.-100° C. with a pressure of only 15 psi, and the process is even possible at room temperature. The reaction is preferably carried out in an inert atmosphere under full or partial hydrogen pressure. Hydrogen pressure should be sufficiently high for hydrogenation and preferably oxygen is absent. Batch or continuous type operations may be used.

The term lower polyhydric alcohols as used for the product of the invention refers to compounds resulting from the hydrocracking of monosaccharides and they predominantly have fewer than five carbon atoms. These lower polyhydric alcohols can include glycols such as ethylene glycol, glycerol, threitol, erythritol, etc. For example, fructose gives glycerol as the primary cleavage product together with small amounts of ethylene glycol. Glucose gives ethylene glycol and glycerol as the primary cleavage products. In addition to lower polyhydric alcohols, the products of the hydrocracking can include methanol, hexitols, $C_3$ and $C_4$ sugars and other products.

The process of the invention shows very high selectivity for ethylene glycol and/or glycerol products over propylene glycol. Products may be separated out by vacuum distillation and/or liquid-liquid extraction, taking advantage of the fact that N-methyl-2-pyrrolidinone and the catalyst are readily soluble in aromatic solvents, while the glycols are not.

EXAMPLES

Sugar, catalyst, and gas chromatography (GC) internal standards (bibenzyl and 1,2-diphenoxyethane) were dissolved in 15 ml N-methyl-2-pyrrolidinone under argon. The desired amount of base (potassium hydroxide 1 M aqueous or anhydrous potassium t-butoxide) was then added with stirring. The resulting solution was transferred to an autoclave under argon and pressurized with hydrogen. The reaction was then typically stirred at 1000 rpm and heated to 100° C. in less than 10 minutes. Product analyses were performed by GC analysis of suitably derivatized reaction aliquotes. Tables I and II give further details of the experimental conditions and yields of the primary products observed. Percent conversions correspond to percent of initial sugar converted to products other than the starting sugar or its isomers. Percent yields of products are weight percent of carbohydrate substrate, i.e. grams of product per gram of starting sugar.

Example 1 illustrates the hydrocracking of carbohydrates such as fructose unexpectedly can be carried out using soluble transition metal hydrogenation catalyst such as $H_2Ru(PPh_3)_4$ alone. Examples 2-4 show the advantageous promoting effect of a strong base co-catalyst such as potassium hydroxide. (Note that data for Examples 2 and 3 are given for times short of complete reaction for comparative purposes). Example 5 illustrates good conversion using a small amount of catalyst. Example 6 demonstrates that hydrocracking can be observed under conditions as mild as 50° C. and 15 psi hydrogen pressure. Example 7 illustrates that different promoters can be used. Examples 8 and 9 provide examples of the hydrocracking of various other sugars. Example 10 illustrates that different hydrocracking catalysts can be used.

While there have been described what are presently believed to be the preferred embodiments of the invention, those skilled in the art will realize that changes and modifications may be made thereto without departing from the spirit of the invention and it is intended to claim all such changes and modifications as fall within the true scope of the invention.

TABLE I

| | Catalytic Hydrocracking of Fructose by $H_2Ru(PPh_3)_4$ in $\underline{N}$-Methyl-2-pyrrolidinone. Effect of Potassium Hydroxide Co-Catalyst | | | | |
|---|---|---|---|---|---|
| Example # | 1 | 2 | 3 | 4 | 5 |
| Fructose | 64 mM | 64 mM | 63 mM | 72 mM | 63 mM |
| $H_2Ru(PPh_3)_4$ | 1.4 mM | 1.9 mM | 1.9 mM | 2.0 mM | 0.5 mM |
| KOH | 0.0 mM | 0.2 mM | 0.9 mM | 4.7 mM | 1.0 mM |
| Temperature | 100° C. | 100° C. | 100° C. | 100° C. | 100° C. |
| Pressure ($H_2$) | 300 psi | 300 psi | 300 psi | 300 psi | 300 psi |
| Time | 24 h | 2.0 h | 1.7 h | 1.5 h | 23 h |
| Conversion | 83% | 70% | 76% | 92% | 78% |
| Ethylene Glycol | 1% | 2% | 4% | 8% | 4% |
| Glycerol | 15% | 25% | 26% | 36% | 31% |

TABLE I-continued

Catalytic Hydrocracking of Fructose by $H_2Ru(PPh_3)_4$ in N-Methyl-2-pyrrolidinone. Effect of Potassium Hydroxide Co-Catalyst

| Example # | 1 | 2 | 3 | 4 | 5 |
|---|---|---|---|---|---|
| Propylene Glycol | 0.2% | 0.1% | 0.2% | 0.6% | 0.4% |
| Hexitols | 64% | 18% | 7% | 5% | 9% |

TABLE II

Catalytic Hydrocracking of Sugars in N-Methyl-2-pyrrolidinone. Effect of Other Reaction Variables.

| Example # | 6 | 7 | 8 | 9 | 10 |
|---|---|---|---|---|---|
| Sugar | Fructose 64 mM | Fructose 64 mM | Glucose 64 mM | Manno-heptulose 64 mM | Fructose 65 mM |
| Catalyst (L=PPh$_3$) | $H_2RuL_4$ 2.0 mM | $H_2RuL_4$ 1.9 mM | $H_2RuL_4$ 1.9 mM | $H_2RuL_4$ 2.1 mM | $H_2Ru(CO)L_3$ 1.9 mM |
| Base | KOH 1.0 mM | KO-t-Bu 4.9 mM | KOH 1.9 mM | KOH 0.2 mM | KOH 1.0 mM |
| Temperature | 50° C. | 100° C. | 100° C. | 100° C. | 100° C. |
| Pressure (H$_2$) | 15 psi | 300 psi | 300 psi | 300 psi | 300 psi |
| Time | 24 h | 1.5 h | 2.0 h | 7.0 h | 7.0 h |
| Conversion | 48% | 97% | 85% | 66% | 81% |
| Ethylene Glycol | 2% | 8% | 6% | 1% | 5% |
| Glycerol | 6% | 38% | 11% | 13% | 27% |
| Tetritols | 2% | 9% | 8% | 17% | 7% |
| Hexitols | 2% | 3% | 20% | 1% | 5% |

What is claimed is:

1. A process for hydrocracking a monosaccharide, a disaccharide, or a pretreated polysaccharide substrate, or a mixture of such substrates, which comprises bringing the substrate into contact with hydrogen in a solution containing a soluble Group VIII metal hydrogenation catalyst selected from the group consisting of $H_2Ru(PPh_3)_4$; $H_2Ru(CO)(PPh_3)$; $H_3Ru(PPh_3)_3{}^{-1}$; $H_3Ir(PPh_3)_3$; $HMX(CO)(PPh_3)_n$ wherein M=Ru or Os, X is selected from the group consisting of Cl, Br and $CH_3CO_2$, and n=2 or 3; $HRh(PPh_3)_4$; and $H_2Rh(PPhMe_2)_2(solvent)_2{}^{+1}$.

2. The process of claim 1 wherein the solution also contains a strong base.

3. The process of claim 2 wherein the base is selected from the group consisting of alkali metal hydroxides, alkoxides and basic salts and alkaline earth metal oxides, alkoxides, hydroxides and basic salts.

4. The process of claim 2 wherein the base is present in an amount of from about 0.01 to about 25 mole percent of the substrate.

5. The process of claim 1 wherein the soluble Group VIII metal hydrogenation catalyst is present in an amount of from about 0.001 to about 10 mole percent of the substrate.

6. The process of claim 1 wherein the solution is in a polar solvent capable of dissolving the substrate and the catalyst.

7. The process of claim 6 wherein the solvent is an amide.

8. The process of claim 7 wherein the solvent is N-methyl-2-pyrrolidinone or N,N-dimethylacetamide.

9. The process of claim 6 wherein the catalyst has been rendered water soluble and the solvent is water.

10. The process of claim 1 wherein the process is carried out at a temperature of between about 50° C. and about 150° C.

11. The process of claim 1 wherein the process is carried out at a hydrogen pressure of between about 15 and about 3000 psi.

12. A process for the production of lower polyhydric alcohols comprising contacting a monosaccharide substrate with hydrogen in the present of a soluble transition metal catalyst selected from the group consisting of $H_2Ru(PPh_3)_4$; $H_2Ru(CO)(PPh_3)_3$; $H_3Ru(Ph_3)^{-1}$; $H_3Ir(PPh_3)_3$; $HMX(CO)(PPh_3)_n$ wherein M=Ru or Os, X is selected from the group consisting of Cl, Br and $CH_3CO_2$, n=2 or 3; $RhCl(PPh_3)_3$; $HRh(PPh_3)_4$; $H_2Rh(PPhMe_2)_2(solvent)^{+1}{}_2$ and $RuCl_2(PPh_3)_3$ and a strong base at a temperature of from about 75° C. to about 125° C. and a pressure of about 100 to about 500 psi is in an amide solvent for about 1 to 12 hours in the absence of oxygen.

13. The process of claim 12 wherein the soluble transition metal catalyst is $H_2Ru(PPh_3)_4$ or $H_2Ru(CO)(PPh_3)_3$.

14. The process of claim 12 wherein the solvent is N-methyl-pyrrolidinone or N,N-dimethylacetamide.

* * * * *